United States Patent [19]

Miller et al.

[11] Patent Number: 4,905,267
[45] Date of Patent: Feb. 27, 1990

[54] METHOD OF ASSEMBLY AND WHOLE BODY, PATIENT POSITIONING AND REPOSITIONING SUPPORT FOR USE IN RADIATION BEAM THERAPY SYSTEMS

[75] Inventors: Daniel W. Miller, Yucaipa; Thomas M. Potts, Grand Terrace, both of Calif.; Rudolf E. Prechter, Cranbury; Benjamin A. Prichard, Jr., East Windsor, both of N.J.; James M. Slater, Redlands, Calif.

[73] Assignee: Loma Linda University Medical Center, Loma Linda, Calif.

[21] Appl. No.: 187,722

[22] Filed: Apr. 29, 1988

[51] Int. Cl.$^4$ .................................. H05G 1/00
[52] U.S. Cl. ................................. 378/208; 378/68; 378/69; 378/209
[58] Field of Search ............... 378/64, 65, 68, 205, 378/208, 209, 180, 69; 5/82 R, 446, 464

[56] References Cited

U.S. PATENT DOCUMENTS

| 2,469,084 | 5/1949 | Schenker | 5/464 |
| 3,545,739 | 12/1970 | D'Avignon | 378/180 |
| 3,689,949 | 9/1972 | Weinstein et al. | 5/60 |
| 3,778,049 | 12/1973 | Viamonte Jr. | 378/209 |
| 3,848,132 | 11/1974 | Foderaro | 378/209 |
| 3,885,258 | 5/1975 | Regan | 5/464 |
| 3,893,198 | 7/1975 | Blair | 5/446 |
| 3,905,054 | 9/1975 | Windsor et al. | 5/81 R |
| 3,947,686 | 3/1976 | Cooper et al. | 378/209 |
| 4,671,284 | 6/1987 | Wilson et al. | 5/60 |
| 4,682,818 | 7/1987 | Morell | 5/464 |

FOREIGN PATENT DOCUMENTS

| 2513896 | 10/1975 | Fed. Rep. of Germany | 5/446 |
| 7309246 | 10/1974 | Netherlands | 5/446 |
| 0870225 | 6/1961 | United Kingdom | 378/180 |

OTHER PUBLICATIONS

"Alpha Cradle", advertisement by Smithers Medical Products, Inc., received by Applicants in 1988.
"Radiobiology for the Radiologist", by Hall, 3rd ed., published by J. B. Lippincott Company, Philadelphia, pp. 275–291, 1988.

Primary Examiner—Craig E. Church
Assistant Examiner—John C. Freeman
Attorney, Agent, or Firm—Robert R. Meads

[57] ABSTRACT

A whole-body patient positioning and repositioning support for fixedly securing a patient in an original position during radiation treatment and for repositioning the patient to the same original position for subsequent radiation treatments. The support includes a foamed-in-place mold within a disposable plastic shell carrying a grid of radio-opaque members for generating a patient registration grid on X-rays for use in the evaluation and adjusting of the position of the patient to the original position using a sheet or straps between the patient and the mold.

13 Claims, 1 Drawing Sheet

METHOD OF ASSEMBLY AND WHOLE BODY, PATIENT POSITIONING AND REPOSITIONING SUPPORT FOR USE IN RADIATION BEAM THERAPY SYSTEMS

BACKGROUND

The present invention relates to radiation beam therapy systems and more particularly to a patient support for positioning and repositioning a patient in the exact same position for successive radiation treatments.

United States Patent Application Serial No. 07/163,611, filed Mar. 3, 1988, and assigned to the Loma Linda University Medical Center, describes and illustrates a radiation beam therapy system. The Loma Linda system includes several different treatment stations each including a gantry for supporting and rotating a radiation beam transport and delivery system on an axis of rotation around a stationary patient to deliver a treatment beam to a predetermined target isocenter within the patient from several different angles. The radiation beam described in the patent application is a highly concentrated proton beam which may be focused to release substantially all of its energy at predetermined isocenters within a target range of 1 mm. Because of the high beam concentration and energy release control provided by the Loma Linda system, it is ideally suited for the treatment of cancer patients wherein proton beams are precisely focused at and irradiate diseased tissue without damaging surrounding healthy tissue.

With the Loma Linda system, a unique treatment plan is first developed for each cancer patient. In the development of a treatment plan, the patient may be positioned on a support table and the internal anatomy of the patient's body scanned as with a computed tomography device (CT Scanner). Images produced by the CT Scanner are analyzed to precisely locate the cancer sites defining the targets for the proton beams. Following the diagnostic CT study, examining physicians develop a radiation treatment plan calling for a number of different patient treatment sessions with proton beams of different magnitude, duration and direction. For each radiation treatment, it is important that the patient be supported in the exact same position as during the CT study utilized in the development of the treatment plan ("original position").

In the above referenced patent application, the patient support is diagrammatically illustrated as comprising a table. While a table may be moved vertically and laterally to position a patient, alone it is not capable of exactly repositioning a patient to the original position within a range of about 1 mm as required by the Loma Linda system. Accordingly, there is a need for a patient positioning and repositioning support for fixedly securing a patient in an original position during radiation treatment and for repositioning the patient in the same original position during subsequent radiation treatments. For radiation treatment systems, such as the Loma Linda system, which are designed to irradiate different portions of a patient's anatomy from several different angles, it is desired that the patient positioning and repositioning support fixedly secure the patient in a supine position. This requires that the whole body of the patient be fixedly supported.

Heretofore, patient positioning and repositioning supports have most commonly supported only predetermined portions of a patient's body. Whole body supports have been relatively complex, expensive and have not been capable of the precise patient repositioning required by proton therapy systems.

An example of a support system for predetermined patient body portions is the ALPHA CRADLE MOLD MAKER marketed by Smithers Medical Products Inc. of Akron, Ohio. In the Alpha Cradle system, a flat board having an open grid pattern of grooves is laid on a horizontal table. A plastic bag included in the system is opened and a foaming agent poured into the bag. The bag is then laid on top of the board and the foaming agent smoothed within the bag. Next, a patient is positioned on the table with a predetermined body portion, e.g. head and neck, resting on top of the bag. As the foaming agent expands, a technician shapes the bag about the body portion and blocks the bag against lateral expansion by placing small vertical wall members in the grooves along marginal edges of the bag. The patient lies motionless for about 15 minutes until the foam has cooled to room temperature and a solid mold of the body portion formed by the foam within the bag. Then the body portion may be removed from the mold which is now suitable for use in positioning and repositioning the body portion for successive radiation treatments. Patient positioning and repositioning supports similar to the Alpha Cradle system are employed at the Harvard Cyclotron Laboratory in association with Massachusetts General Hospital in Boston, Massachusetts.

A whole body support system has been employed by the Swiss Institute for Nuclear Research (SIN). The SIN system includes rigid fiberglass semi-cylindrical bottom and top portions forming a cylindrical tube for positioning a patient. The cylindrical tube is intended to be reused for different patients. To support the body of a patient within the cylindrical tube, the SIN system includes a number of rigid foam inserts each have a shape conforming somewhat to different portions of a patient's body. By selectively positioning a number of the inserts within the bottom semi-cylinder, a mold is formed which approximates the general shape of a back-side of a patient. A plastic liner is placed over the mold and a foaming agent introduced under the liner for foaming while the patient lies thereon. The result is a whole body mold which conforms closely to the shape of the back-side of the patient and which may be used in the positioning and repositioning of the patient within the cylindrical tube for radiation treatments. The SIN system utilizes a radiation beam that is rather diffuse. Therefore, it is not critical that the patient be repositioned to exactly the same position for each subsequent radiation treatment and means are not included in the SIN system for exactly repositioning the patient to the original supine position.

Accordingly, a need exists for a whole body patient positioning and repositioning support for fixedly securing a patient in an original supine position during radiation treatment and for repositioning the patient to the same original supine position for subsequent radiation treatments. Preferably, the support should be simple in design, easily assembled, and relatively inexpensive. Further, ideally, the support should incorporate means for readjusting slightly the position of the patient in the support to the original supine position prior to subsequent radiation treatments. The support of the present invention satisfies such needs.

SUMMARY OF INVENTION

Generally speaking, the whole body patient positioning and repositioning support of the present invention comprises a rigid, longitudinally extending base member for support on a moveable transport. The base member includes a transverse slightly concave top surface. A disposable, relatively thin, longitudinally extending, plastic shell is releasably secured to and supported by the base member with a transverse convex bottom of the shell nested in the concave top of the base member and a transverse concave top surface of the shell exposed to receive a thin flexible plastic liner. The liner overlies the shell and a rigid foam is bonded to the shell and to the liner to comprise a mold conforming exactly to the back-side of the patient for securely holding the patient in an original supine position during radiation treatments. Preferably, the whole body support includes moveable means such as a sheet or straps between the liner and the patient lying on the support for readjusting slightly as necessary the position of the patient to the original supine position prior to subsequent radiation treatments. Further, the support includes a grid of radio-opaque members preferably carried by the shell for generating a registration grid on x-rays of the patient on the support for use in evaluation and adjustment of the position of the patient on the support. Such x-rays may be used in conjunction with the moveable means for slightly readjusting of the patient to insure that the patient is exactly in the same original supine position for each subsequent radiation treatment.

The method of assembly of the support is simple and comprises the steps of securing the shell to the base member with the convex bottom of the shell nested in the concave top of the base member and generating a foam on the inner surface of the shell and under the liner while positioning a patient in a supine position on top of the liner. When the foam expands and hardens it forms a whole body mold for a bottom side of the patient. Moveable means are then placed over the top of the liner for lying under the patient. The moveable means may be manually or mechanically gripped during the operation of adjusting slightly the position of the patient within the mold.

DETAILED DESCRIPTION OF INVENTION

Figure 1:
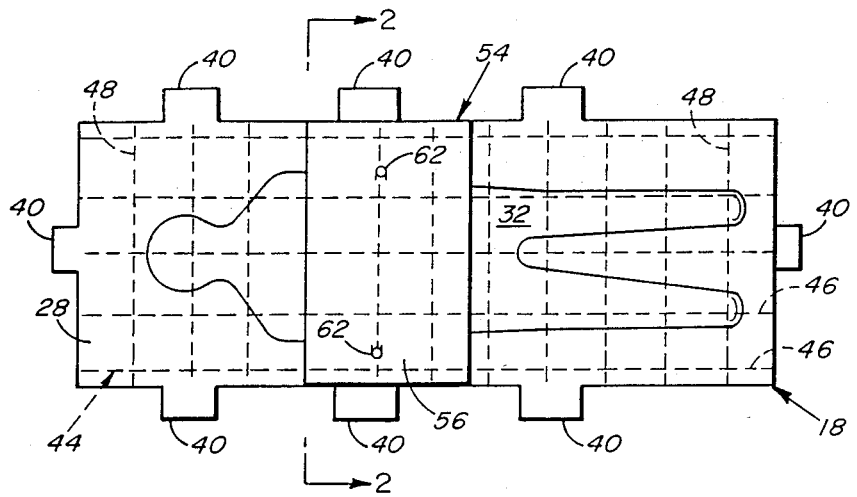
FIG. 1 is a top view of the support of the present invention.

In the drawings, the support is represented generally by the numeral 10. It comprises a rigid, longitudinally extending base member 12. The base member is designed for support on a moveable transport such as a moveable cart (not shown). To this end, a longitudinally extending groove member 14 of a tongue and groove combination is secured to a transversely convex bottom most side 15 of the base member 12. The upper side 16 of the base member 12 is slightly concave in a direction transverse to the longitudinal direction of the base to support a relatively thin, longitudinally extending disposable plastic shell 18. The shell is releasibly secured to the base member 12 as by a plurality of longitudinally spaced vertically extending pins 20 fitted into corresponding holes 22 in the concave top surface 16 of the base member. Preferably, the shell 18 includes a transversely concave top surface 24 and a transversely convex bottom 26 for nesting in the concave top 16 of the base member 12.

A thin flexible plastic liner 28, such as a thin foam blanket or plastic foil overlies the shell 18. The liner 28 is designed to form the top surface of a hole body mold for the back-side of a patient lying in a supine position on the support 10. In these regards, a rigid foam 30 is bonded to and between the shell 18 and an underside of the liner 28 and comprises a mold 32 conforming exactly to the back-side of the patient for securely holding the patient in an original supine position during radiation treatments. The rigid foam 30 may be formed in a manner similar to that employed in the Alpha Cradle Mold Maker using a liquid foaming agent known as ACMM foaming agent 325 available from Smithers Medical Products Inc., Akron, Ohio. The foaming agent may be painted onto the concave top surface 24 of the shell 18 and the liner 28 positioned over the shell or the foaming agent may be introduced through nozzles 34 in the shell between the inner surface of the shell and the liner. In either event, after the foaming agent is introduced within the shell, the patient is positioned within the shell where he or she must lie motionless for about 15 minutes until the foaming agent has cooled to room temperature and the hole body mold 32 formed.

Figure 2:
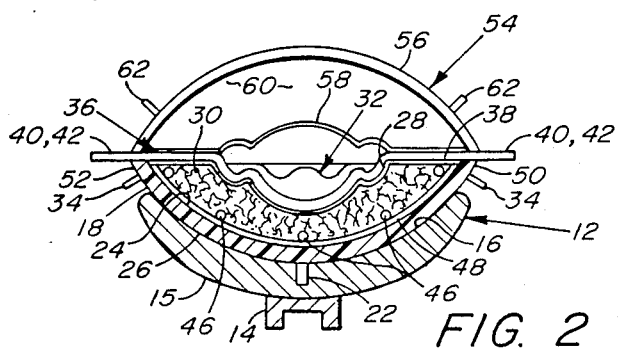
FIG. 2 is a sectional side view taken along the line 2—2 in FIG. 1.
Figure 3:
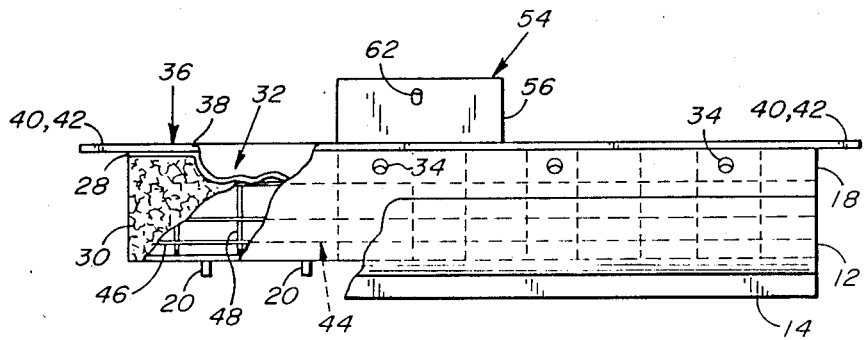
FIG. 3 is a side view of the support illustrated in FIG. 1 with portions broken away to expose the inner structure of the support.

As previously mentioned, it is important that the patient be repositioned within the mold 32 to the exact original supine position during subsequent radiation treatments. To insure that the patient is so repositioned, the support of the present invention preferably includes moveable means 36 such as a sheet 38 between the liner 28 and the patient lying on the support. Portions of the sheet defining laterally extending and exposed handle portions 40 extend outwardly beyond the sides and the ends of the shell 18 for manual or mechanical gripping during a transfer of longitudinal and/or lateral patient moving forces to the sheet as required to slightly move the patient within the mold to the original supine position. Alternatively, a number of straps such as 42 in the FIG. 2 may be placed under the patient within the mold for the same purpose.

To aid in the accurate positioning and repositioning of the patient within the mold 32, the support of the present invention preferably includes a grid 44 of radio-opaque members carried by the shell 18 for generating a registration grid on x-rays of the patient on the support. Such x-rays taken after a patient has been repositioned on the support are compared with x-rays of the patient in the original supine position on the support. By comparing the x-ray the need for slight position adjustment is determined and by operation of the moveable means 36, the patient is moved to the exact original supine position.

Preferably, the grid 44 is formed by laterally separated longitudinally extending radio-opaque strips 46 and crossing longitudinally separated laterally extending radio-opaque strips 48. As illustrated, the laterally extending strips 48 and some of the longitudinally extending strips 46 are carried by opposing side wall 50 and 52 of the shell whereby the strips when looking from a top of the support and from a side of the support define biplanar grid patterns.

Preferably, the support of the present invention further includes a concave top cover 54 resting on opposing sides of the shell 18 and the rigid foam 30 over a portion of the patient's body which is to receive radiation treatment. The top cover comprises an outer concave top shell 56 of a thin plastic material, a top plastic liner 58 between the top shell and a top side of the patient within the mold, and a top rigid foam 60 between the top shell and the top liner forming a mold conforming to a top side of the patient under the cover 54. The foam 60 may be formed to such a mold during the process of forming the mold 32 by applying a foaming agent to the under side of the top shell 56 while the patient is positioned between the bottom and top liners 28 and 58. Alternatively, the foaming agent forming the foam 60 may be introduced into the top cover through nozzles 62 carried by the top shell 56.

With the support 10 as described, the method of assembling a whole body positioning support for use in radiation diagnosis and treatment comprises the steps of securing the shell 18 to the rigid base 12 with the convex bottom of the shell nested in a concave top of the base. A foaming agent then is applied to the inner surface of the shell and under the liner 28 and a patient positioned in a supine position on the liner while the foam expands and hardens to complete the whole body mold 32. With the mold 32 formed as indicated, the sheet 38 or straps 42 are placed on top of the liner 28 for positioning under the patient to define the patient moving means 36 for slightly moving the patient as needed to an original supine position in the mold 32 for each radiation treatment. Finally, the method includes the step of covering the portion of the patient's body to receive radiation with the top cover 54.

While a preferred form of the support of the present invention and its method of assembly have been described as supporting patients in a supine position, the support 10 may be assembled to support patients in prone and other positions. Of course, in the prone position, the mold 32 will conform to the front side of a patient's body with breathing holes provided for the patient and the top cover 54 will be assembled to define a mold for the back side of a patient's body.

We claim:

1. A whole-body patient positioning and repositioning support for fixedly securing a patient in an original position during radiation treatment and for repositioning the patient to the same original position for subsequent radiation treatments, the support comprising:
   a rigid, longitudinally extending base member for support on a moveable transport, the base member having a transverse slightly concave top surface;
   a relatively thin, longitudinally extending, shell releasably secured to and supported by the base member with a transverse convex bottom of the shell nested in the concave top of the base member and a transverse concave top surface of the shell exposed to receive a liner;
   interlocking means between the shell and the base member;
   a thin flexible plastic liner overlying the shell; and
   a rigid foam between and bonded to the shell and the liner and comprising a mold conforming exactly to a side of the patient for securely holding the patient in the original position during radiation treatments.

2. The support of claim 1 further including patient moving means between the liner and a patient lying on the support for manually readjusting the position of the patient to the original position prior to subsequent radiation treatments.

3. The support of claim 2 wherein the patient moving means comprises a sheet of material underlying the patient in the mold with laterally extending and exposed handle portions for manually or mechanically gripping during a transfer of longitudinal and/or lateral patient moving forces to the sheet.

4. The support of claim 2 wherein the patient moving means comprises laterally extending straps under the patient for manually or mechanically gripping during a transfer of longitudinal and/or lateral patient moving forces to the straps.

5. A whole-body patient positioning and repositioning support for fixedly securing a patient in an original position during radiation treatment and for repositioning the patient to the same original position for subsequent radiation treatments, the support comprising:
   a rigid, longitudinally extending base member for support on a moveable transport, the base member having a transverse slightly concave top surface;
   a relatively thin, longitudinally extending shell releasably secured to and supported by the base member with a transverse convex bottom of the shell nested in the concave top of the base member and a concave top surface of the shell exposed to receive a liner;
   a thin flexible liner overlying the shell;
   a rigid foam between and bonded to the shell and the liner and comprising a mold conforming exactly to a side of the patient for securely holding the patient in the original position during radiation treatments; and
   a grid of radio-opaque members carried by the support for generating a registration grid on X-rays of the patient on the support for use in evaluation and adjusting the position of the patient on the support.

6. The support of claim 5 wherein the grid is formed by laterally separated longitudinally extending radio-opaque strips and crossing longitudinally separated laterally extending radio-opaque strips carried by the shell.

7. The support of claim 6 wherein the laterally extending and some of the longitudinally extending strips are carried by opposing side wall portions of the shell whereby the strips define a biplanar grid pattern.

8. The support of claim 5 further including a concave top cover resting on opposing sides of the shell and the rigid foam over a portion of the patient's body which is to receive radiation treatment, the cover comprising an outer concave top shell, a top liner between the top shell and a top side of the patient and a top rigid foam between the top shell and the top liner and forming a mold conforming to a top side of the patient under the cover.

9. A method of assembling a whole body patient positioning support for use in radiation diagnosis and treatment, the method comprising the steps of:
   placing a thin, longitudinally extending, shell on a longitudinally extending, rigid base member with a transverse convex bottom surface of the shell nested in a transverse concave top surface of the base member and a transverse concave top surface of the shell exposed to receive a liner;
   interlocking the shell and base with interlocking means;
   applying a foaming agent to the top surface of the shell and under a liner overlying the shell; and positioning a patient on the liner while the foam expands and hardens to complete a whole body mold for a bottom side of the patient.

10. A method of positioning a patient for radiation treatment, comprising:
   securing to a base member a foamed-in-place mold of a portion of a patient's body,
   placing patient moving means on the mold and under the patient and
   as needed slightly moving the patient with such means to an original position in the mold.

11. A method of assembling a whole body patient positioning support for use in radiation diagnosis and treatment, the method comprising the steps of:
   securing a thin, longitudinally extending shell to a longitudinally extending, rigid base member with a transverse convex bottom surface of the shell nested in a transverse concave top surface of the base member and a transverse concave top surface of the shell exposed to receive a liner;
   applying a foaming agent to the top surface of the shell and under a liner overlying the shell;
   positioning a patient on the liner while the foam expands and hardens to complete a whole body mold for a bottom side of the patient; and
   covering a portion of the patient's body to receive radiation treatment with a top cover having a thin outer concave top shell, a top liner and a rigid foam between the top shell and top liner conforming to the top body shape of the body portion to receive radiation treatment.

12. In a support for fixedly securing at least a portion of a patient's anatomy during radiation treatment, a combination of:
   a foamed-in-place mold for receiving and fixedly securing a portion of a patient's body in an original position; and
   a grid of radio-opaque members in the support adjacent the mold for generating a registration grid in X-rays of the patient in the mold for use in evaluating and adjusting the position of the patient in the mold to insure that the patient is repositioned to the original position prior to each sucessive radiation treatment.

13. The combination of claim 12, further including patient moving means between the mold and the patient in the mold for adjusting slighty the position of the patient as necessary to bring the patient to the original position in the mold prior to each sucessive radiation treatment.

* * * * *

Disclaimer 4,905,267—Daniel W. Miller, Yucaipa; Thomas M. Potts, Grand Terrace, both of Calif.; Rudolf E. Prechter, Cranbury; Benjamin A. Prichard, Jr., East Windsor, both of N.J.; James M. Slater, Redlands, Calif. METHOD OF ASSEMBLY AND WHOLE BODY, PATIENT POSITIONING AND REPOSITIONING SUPPORT FOR USE IN RADIATION BEAM THERAPY SYSTEMS. Patent dated Feb. 27, 1990. Disclaimer filed April 17, 1997, by the assignee, Loma Linda University Medical Center.

Hereby enters this disclaimer to claims 1, 9 and 11 of said patent.
*(Official Gazette,* August 12, 1997)